US008828403B2

(12) United States Patent
Filaci et al.

(10) Patent No.: US 8,828,403 B2
(45) Date of Patent: Sep. 9, 2014

(54) ANTI-TUMOR IMMUNOTHERAPY

(75) Inventors: Gilberto Filaci, Genoa (IT); Francesco Indiveri, Genoa (IT); Paolo Traverso, Genoa (IT)

(73) Assignee: Mediolanum Farmaceutici S.p.A., Milan (IT)

( * ) Notice: Subject to any disclaimer, the term of this patent is extended or adjusted under 35 U.S.C. 154(b) by 479 days.

(21) Appl. No.: 12/997,630

(22) PCT Filed: Jun. 16, 2009

(86) PCT No.: PCT/EP2009/004337
§ 371 (c)(1),
(2), (4) Date: Jan. 26, 2011

(87) PCT Pub. No.: WO2010/003520
PCT Pub. Date: Jan. 14, 2010

(65) Prior Publication Data
US 2011/0135692 A1        Jun. 9, 2011

Related U.S. Application Data

(60) Provisional application No. 61/061,778, filed on Jun. 16, 2008.

(51) Int. Cl.
*A61K 38/00*     (2006.01)
*A61K 38/03*     (2006.01)
*A61K 39/00*     (2006.01)
*A61K 45/00*     (2006.01)
*A61K 47/44*     (2006.01)
*A61K 38/45*     (2006.01)
*C12N 9/12*      (2006.01)
*C07K 14/00*     (2006.01)

(52) U.S. Cl.
CPC .............. *A61K 38/45* (2013.01); *C12N 9/1241* (2013.01)
USPC .................. 424/185.1; 424/277.1; 424/278.1; 424/283.1

(58) Field of Classification Search
None
See application file for complete search history.

(56) References Cited

U.S. PATENT DOCUMENTS

| 7,030,211 | B1 | 4/2006 | Gaudernack et al. |
| 7,301,027 | B2 * | 11/2007 | Colombo et al. ............... 546/82 |
| 7,794,723 | B2 | 9/2010 | Gaudernack et al. |
| 2006/0106196 | A1 | 5/2006 | Gaudernack et al. |

FOREIGN PATENT DOCUMENTS

| WO | 00/02581 A1 | 1/2000 |
| WO | 02/070679 A2 | 9/2002 |
| WO | 03/038047 A2 | 5/2003 |

OTHER PUBLICATIONS

Kessler and Melief (Leukemia, 2007, 21: 1859-1874).*
Engelhard (Curr. Opin. Immunol. 1994, 6: 13-23).*
Guo et al (Nature, 1992, 360: 364-366).*
Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
Parmiani et al (Ann. Oncol., 2007, 18: 226-232).*
Lingnau et al (Expert. Rev. Vacc. 2007, 741-746).*
Aucouturier et al (Exp. Rev. Vacc. 2002, 1: 111-118).*
Rosenberg et al (J. Immunotherapy, 2010, 33(6): 626-629).*
Su, Zhen, et al., "Telomerase mRNA-Transfected Dendritic Cells Stimulate Antigen-Specific CD8+ and CD4+ T Cell Responses in Patients with Metastatic Prostate Cancer," Journal of Immunology, Mar. 15, 2005, vol. 174, No. 6, pp. 3798-3807, Baltimore, MD; dated May 12, 2010, issued in corresponding PCT/EP2009/004337.
Carpenter, Erica, et al., "Telomerase-based immunotherapy of cancer," Expert Opinion on Biological Therapy, Informa Healthcare, UK, Oct. 1, 2006, vol. 6, No. 10, pp. 1031-1039; dated May 12, 2010, issued in corresponding PCT/EP2009/004337.
Brunsvig, P., et al., "Telomerase peptide vaccination: a phase I/II study in patients with non-small cell lung cancer," Cancer Immunology, Immunotherapy, Feb. 21, 2006, vol. 55, No. 12, pp. 1553-1564, Springer-Verlag 2006, Berlin, Germany; dated May 12, 2010, issued in corresponding PCT/EP2009/004337.
International Search Report, dated May 12, 2010, issued in corresponding PCT/EP2009/004337.
Written Opinion of the International Searching Authority, dated May 12, 2010, issued in corresponding PCT/EP2009/004337.

* cited by examiner

*Primary Examiner* — Gerald R Ewoldt
*Assistant Examiner* — Marianne Dibrino
(74) *Attorney, Agent, or Firm* — Lucas & Mercanti, LLP

(57) ABSTRACT

The present invention relates to the use of telomerase-derived peptides for the treatment of any cancer patients, particularly for the treatment of patients with renal or prostate cancer.

10 Claims, No Drawings

ANTI-TUMOR IMMUNOTHERAPY

This application is a U.S. national stage of PCT/EP2009/004337 filed on Jun. 16, 2009, which claims priority to and the benefit of U.S. Provisional Application Ser. No. 61/061,778 filed Jun. 16, 2008, the contents of which are incorporated herein by reference in their entirety.

The present invention relates to the use of telomerase-derived peptides for the treatment of any cancer patients, particularly for the treatment of patients with renal or prostate cancer.

Renal cell carcinoma (RCC) represents the 3% of tumors in adults and its incidence increases at a rate of 1.5-5.9% per year. The mortality rate for this disease is increasing proportionally to the augment of incidence. About 25-30% of patients has advanced, metastatic disease at diagnosis, and several patients without clinical evidence of metastasis at the time of diagnosis have already disseminated micrometastases. This is responsible for the poor efficacy of actual therapeutic approaches and for the low survival rates (0-13% of metastatic patients survive after 5 years from diagnosis).

Prostate cancer is a major medical problem. In Europe there are 2.6 millions of new cases every year. It constitutes the 11% of tumor cases in males, and it is responsible for the 9% of deaths due to cancer in Europe. Moreover, its incidence in male population is the double of that of lung cancer; prostate cancer constitutes the 30% of new neoplasia cases in males with a elevated mortality rate.

At diagnosis the 45% of patients has already an advanced disease with a survival rate <50% at five years independently from the type of therapeutic approach.

Telomerase is the reverse transcriptase of eukaryotic cells required for the synthesis of the telomeric regions of chromosomes. Telomerase is present in embryonic but not in adult somatic cells with few exceptions constituted by germinal cells and actively proliferating cells. However, the rate of telomerase expression in these cells is so low that telomerase cannot be recognized by telomerase-specific cytotoxic lymphocytes (CTL). Telomerase is essential for cell immortalization: this explains why it is expressed by about 90% of tumours (independently on the histological type). For this reason, telomerase is now considered a potential "universal" tumor antigen. This view is further supported by the finding that cytotoxic T lymphocytes (CTL) able to kill cancer cells through the specific recognition of peptides derived from the catalytic subunit of the human telomerase reverse transcriptase (hTERT) have been identified in the peripheral blood of both healthy subjects and cancer patients. In particular, about 90% of cancer patients have telomerase-specific CTL.

On this basis, clinical trials have been performed (or are ongoing) to analyze the safety and the immunological effects of immunization of cancer patients with single telomerase peptides or a combination of 2 telomerase peptides. These trials have demonstrated that telomerase immunization is a safe procedure. In particular, no toxicity on hematopoietic stem cells has been detected (Vonderheide R H, et al. Vaccination of cancer patients against telomerase induces functional antitumor CD8+ T lymphocytes. Clin Cancer Res 2004; 10:828-839. Danet-Desnoyers G H, et al. Telomerase vaccination has no detectable effect on SCID-repopulating and colony-forming activities in the bone marrow of cancer patients. Exp Hematol 2005; 33:1275-1280. Brunsvig P F, et al. Telomerase peptide vaccination: a phase I/II study in patients with non-small cell lung cancer. Cancer Immunol Immunother. 2006; 55:1553-1564). Further telomerase-specific immune responses were induced in several cancer patients. However, although different experimental approaches have been applied partial or complete clinical responses have been obtained only in a minority of treated patients.

The present inventors have now found that an accurate selection of immunogenic peptides and an efficient adjuvant are mandatory for the development of efficient telomerase peptide-based immunotherapy protocol. According to the present invention, a composition comprising a plurality of telomerase-derived peptides is administered for presentation by antigen-presenting cells. This composition comprises both HLA class I and HLA class II restricted peptides. The availability of telomerase epitopes restricted by HLA class I or II molecules and, hence, recognized by CD8+ or CD4+ T lymphocytes, respectively, has great importance since provide the chance to design protocol of active immunization potentially mimicking a fully physiological immune response. In fact, it has been demonstrated that an immune response characterized by the activation not only of tumour-specific CTL but also of tumour-specific CD4+ T cells is essential to achieve efficient anti-tumour effects. This is due to the fact that CD4+ T cells are responsible for processes of induction, regulation and maintenance of CTL-mediated immune responses, as well as of direct anti-tumour killing. A molecular feature of telomerase-derived epitopes restricted by HLA class II molecules is their promiscuity, that is their capacity to bind and be presented by different HLA class II alleles. This is a great advantage in designing an immunotherapic protocol since it allows that single peptide epitopes may be efficiently used to immunize individuals bearing different HLA haplotypes. Thus, a great number of patients might be responsive to immunization with a suitable combination of telomerase-derived peptides.

In a first aspect, the present invention refers to a composition of at least 3 peptides from a mammalian telomerase, particularly from human telomerase, comprising:
(i) at least one HLA class I restricted peptide and
(ii) at least two HLA class II restricted peptides.

The peptide composition of the present invention comprises at least three peptides, e.g. three, four, five or even more peptides. Preferably, the composition comprises four peptides. More preferably, the composition comprises one HLA class I restricted peptide and at least two, particularly at least three HLA class II restricted peptides. The HLA class I restricted peptide is preferably a HLA-A2 restricted peptide. The HLA class II restricted peptides are preferably HLA-DR1, -DR4, -DR7, -DR15, -DP4 and -DQ4 restricted peptides. HLA class I restricted peptides preferably have a length of about 7 to about 11 amino acids, e.g. about 9 amino acids, and HLA class II restricted peptides preferably have a length of about 12 to about 18 amino acids, e.g. about 15 amino acids.

Preferably the peptides of the composition are present in a single container. The amount of each peptide in the composition is usually of from 100-1000 µg, preferably from 200-800 µg, and more preferably from 400-600 µg. Most preferably, each peptide is present in about the same amount e.g. in an amount of about 500 µg.

The HLA class I restricted peptide (i) preferably comprises the amino acid sequence ILAKF LHWL (SEQ ID NO:1) corresponding to amino acids 540-548 of human telomerase. However, any telomerase-derived peptide able to bind to any gene product of an HLA class I allele and to induce activation of peptide-specific CTLs is to be considered suitable for the specific use included in the present invention. The HLA class II restricted peptides (i) are preferably selected from peptides comprising the amino acid sequences RPGLL GASVL GLDDI (SEQ ID NO:2) corresponding to amino acids 672-686 of human telomerase, LTDLQ PYMRQ FVAHL (SEQ ID NO:3) corresponding to amino acids 766-780 of human telomerase, and EARPA LLTSR RFIPK (SEQ ID NO:4) corresponding to amino acids 611-626 of human telomerase. However, any telomerase-derived peptide able to bind to any gene product of any HLA class II allele and to induce activation of peptide-specific CD4+ T lymphocytes is to be considered suitable for the specific use included in the present invention.

The peptides may be synthesized according to known methods, e.g. by solid phase synthesis techniques. If desired, the peptides may comprise N- and/or C-terminal modifications such as acylation or amidation.

In a preferred embodiment of the invention, the peptide composition is administered in combination with an adjuvant, particularly with an adjuvant capable of interacting with toll-like receptors (TLRs) and providing a pro-inflammatory support. In an especially preferred embodiment, the adjuvant is imiquimod, an imidazoquinoline derivative which binds to TLR7 and 8 on human dendritic cells inducing maturation of these cells toward antigen presentation by increasing expression of HLA and co-stimulatory molecules, increasing expression of chemokine receptors such as CCR7 and/or inducing secretion of Th1 cytokines such as IFNγ, IN12 or TFNα. Further preferred adjuvants are agents binding to and/or activating TLRs, such as CpG-containing oligonucleotides. Moreover, the additional use of compounds, such as MONTANIDE™ ISA-51, a vaccine adjuvant, able to reduce the clearance of administered peptides at the site of injection and to exert adjuvant activity, is also part of the invention.

The composition of the present invention is suitable for use in medicine, particularly in human medicine, more particularly as a vaccine for cancer. The composition is useful for the vaccination against any cancer which is telomerase positive. Preferred examples are renal cancer, e.g. renal cell carcinoma, prostate cancer, e.g. prostate adenocarcinoma, but also lung, breast, ovary cancers and lymphomas. The cancer may be in any stage, e.g. in an early stage or in an advanced stage, e.g. at least stage IV.

In a preferred embodiment, the composition is used for administration to a HLA matched human patient, i.e. a human patient who is positive for HLA alleles which correspond to the HLA class I or II alleles which restrict presentation to T lymphocytes of peptides (i) and/or (ii). Especially preferred is an administration to a patient who has been tested to be positive for the HLA-A2 allele corresponding to the preferred HLA class I restricted peptide (i) comprising SEQ. ID NO:1.

The composition of the present invention is administered by any suitable route, e.g. by injection, more particularly by intradermal injection. In order to enhance the immune response, the composition is usually administered together with an adjuvant, e.g. imiquimod.

Further, it is preferred to administer the composition by a protocol comprising a plurality of subsequent administrations, e.g. five or more subsequent administrations. In an especially preferred embodiment, the composition is for administration by a protocol comprising:

1st week: 2-4 times administration, preferably 3 times administration at intervals of about 48 hours,
2nd-4th week: 1-2 weekly administrations, preferably 1 weekly administration,
5th-7th week: 1 administration, preferably 6th week 1 administration,
9th-12th to 12th week: 1 administration, preferably 10th week 1 administration.

Before and after each administration, the adjuvant, e.g. imiquimod, is preferably spread at the administration site for e.g. at least 30 seconds to allow its action.

The administered dose preferably comprises each peptide in about equal amounts, e.g. of about 500 μg.

Further, the present invention is explained in more detail by the following example.

EXAMPLE

Phase I/II Clinical Trial for the Treatment of Patients with Stage IV Renal or Prostate Cancer 1. Inclusion Criteria for Patients Affected with Prostate Cancer
   Histologic diagnosis of prostate adenocarcinoma
   Resistance to hormonal therapy defined as progression after 4 week treatment
   Stage IV of disease
   PSA>10 microg/ml increasing in the last month
   Acceptable liver function defined as: total bilirubin<UNL ("upper normal limit"), AST and ALT<2.5×UNL, alkaline phosphatase<5×UNL
   Acceptable renal function defined as: serum creatinine<1.5×UNL
   Acceptable hematopoietic function defined as: hemoglobin>7 g/l, leukocytes>3×10$^9$/l, platelets>100×10$^9$/l
   Positivity for the HLA-A2 allele
   ECOG performance status<3
   Life expectancy>3 months
   Absence of coexisting immunosuppressive or chemotherapic therapy since 30 days before study onset
   Absence of coexisting autoimmune diseases
   The patient must be able to adhere to protocol requests
   The patient must provide written informed consent
   Age>18 years
2. Inclusion Criteria for Patients Affected with Renal Cancer
   Histologic diagnosis of renal cell carcinoma
   Normal renal function of the non-affected kidney
   Acceptable liver function defined as: total bilirubin<UNL ("upper normal limit"), AST and ALT<2.5×UNL, alkaline phosphatase<5×
   Acceptable hematopoietic function defined as: hemoglobin>7 g/l, leukocytes>3×10$^9$/l, platelets>100×10$^9$/l
   Positivity for the HLA-A2 allele
   ECOG performance status<3
   Life expectancy>3 months
   Male patient
   Female patient not pregnant, not breast feeding and under efficient contraceptive therapy
   Absence of coexisting immunosuppressive or chemotherapic therapy since 30 days before study onset
   Absence of coexisting autoimmune diseases
   The patient must be able to adhere to protocol requests
   The patient must provide written informed consent
   Age>18 years
3. Treatment Protocol
3.1 Telomerase Derived Peptides
   The following immunogenic, telomerase-derived peptides are employed in the study:
   hTERT540-548 (sequence: ILAKFLHWL; restriction: HLA-A2);
   hTERT672-686 (sequence: RPGLLGASVLGLDDI; restriction: HLA-DR1, DR7, DR15);
   hTERT766-780 (sequence: LTDLQPYMRQFVAHL; restriction: HLA-DR4, DR7, DR15);

hTERT611-626 (sequence: EARPALLTSRLRFIPK; restriction: HLA-DP4, DQ4).

3.2 Group Composition

Two groups of patients will be constituted, one for each histologic type of disease. Ten patients per group will be enrolled.

3.3 Treatment

Patients will be treated by active immunotherapy through intradermal injection of the above cited telomerase-derived peptides. A pool of the 4 different peptides will be administered with each injection (500 µg of each peptide per injection). The total injected volume will be 0.4 ml.

Treatment schedule will be as follows:
1st week: 3 intradermal injections at intervals of 48 hours;
2nd-4th weeks: 1 weekly injection;
6th week: 1 injection;
10th week: 1 injection.

Before and after each injection imiquimod (commercial name: ALDARA™) will be spread at the injection site for 30 seconds to allow its absorption.

The invention claimed is:

1. A therapeutic method for the treatment of a cancer expressing human telomerase, comprising the following steps:

A) administering to a subject in need thereof an antitumoral effective amount of 4 peptides from human telomerase wherein said peptides are:
   (i) one HLA class I restricted peptide having the following amino acid sequence ILAKFLHWL (SEQ ID NO. 1),
   (ii) Three HLA class II restricted peptides having the following amino acid sequences: RPGLLGASVLGLDD1 (SEQ ID NO. 2), LTDLQPYMRQFVAHL (SEQ ID. NO. 3) and EARPALLTSRLRFIKP (SEQ ID. NO. 4),
in the form of sterile water/oil emulsion wherein the oil component is an adjuvant and consists of: from 88 to 92% by weight of a white mineral oil identified with the CAS Registry No. 8042-47-5, and from 8 to 12% by weight of mannide monooleate, B) administering to the same subject Imiquimod as a further adjuvant, before, contemporaneously or after (A), at the site wherein respectively step (A) will be, is being or was carried out.

2. The therapeutic method of claim 1, wherein said 4 peptides are administered in the form of a unitary water/oil emulsion containing each peptide in an amount of from 100 to 1000 µg.

3. The therapeutic method of claim 1, wherein said cancer expressing human telomerase is selected from renal cancer and prostate cancer.

4. The therapeutic method of claim 1, wherein said water/oil emulsion is administered by intradermal injection.

5. The therapeutic method of claim 2 wherein said water/oil emulsion is administered by a protocol comprising:
  1$^{st}$ week: 3 intradermal injections at intervals of 48 hours;
  2$^{nd}$-4$^{th}$ week: 1 injection;
  6$^{th}$ week: 1 injection;
  10$^{th}$ week: 1 injection.

6. The therapeutic method of claim 2, wherein said water/oil emulsion contains each peptide in an amount of from 200-800 µg.

7. The therapeutic method of claim 6 wherein said water/oil emulsion contains each peptide in an amount of from 400-600 µg.

8. The therapeutic method of claim 1, wherein said subject is a human patient positive for HLA alleles corresponding to HLA class I or II alleles restricting presentation of said HLA class I and HLA class II restricted peptides.

9. The therapeutic method of claim 8, wherein said human patient, is positive for the HLA-A2 allele.

10. A vaccine for the treatment of a cancer expressing human telomerase comprising as the active ingredients:
  (i) one HLA class I restricted peptide having the following amino acid sequence ILAKFLHWL (SEQ ID NO. 1),
  (ii) three HLA class II restricted peptides having the following amino acid sequences: RPGLLGASVLGLDD1 (SEQ ID NO. 2), LTDLQPYMRQFVAHL (SEQ ID. NO. 3) and EARPALLTSRLRFIKP (SEQ ID. NO. 4),
  in combination with suitable aqueous excipients and/or diluents, said vaccine being associated with the following adjuvants:
  (α) an oily component consisting of: from 88 to 92% by weight of a white mineral hydrocarbon oil identified by the CAS No. 8042-47-5, and from 8 to 12% by weight of a mannide monooleate; and
  (β) Imiquimod.

* * * * *

```
                        SEQUENCE LISTING

<160> NUMBER OF SEQ ID NOS: 4

<210> SEQ ID NO 1
<211> LENGTH: 9
<212> TYPE: PRT
<213> ORGANISM: Homo sapiens

<400> SEQUENCE: 1

Ile Leu Ala Lys Phe Leu His Trp Leu
1               5

<210> SEQ ID NO 2
<211> LENGTH: 15
<212> TYPE: PRT
<213> ORGANISM: Homo sapiens

<400> SEQUENCE: 2

Arg Pro Gly Leu Leu Gly Ala Ser Val Leu Gly Leu Asp Asp Ile
1               5                   10                  15

<210> SEQ ID NO 3
<211> LENGTH: 15
<212> TYPE: PRT
<213> ORGANISM: Homo sapiens

<400> SEQUENCE: 3

Leu Thr Asp Leu Gln Pro Tyr Met Arg Gln Phe Val Ala His Leu
1               5                   10                  15

<210> SEQ ID NO 4
<211> LENGTH: 16
<212> TYPE: PRT
<213> ORGANISM: Homo sapiens

<400> SEQUENCE: 4

Glu Ala Arg Pro Ala Leu Leu Thr Ser Arg Leu Arg Phe Ile Pro Lys
1               5                   10                  15
```